United States Patent [19]

La Londe et al.

[11] 4,007,277
[45] Feb. 8, 1977

[54] PHENYL- AND 1-NAPHTHYL-THIODEOXYNUPHARIDIN-6-α-OLS

[75] Inventors: Robert Thomas La Londe; Amy Inn-Mei Tsai, both of Syracuse; Chun Juan Wang, Jamesville; Chunfook Wong, Syracuse, all of N.Y.

[73] Assignee: Research Corporation, New York, N.Y.

[22] Filed: Jan. 31, 1975

[21] Appl. No.: 546,143

[52] U.S. Cl. .......................... 424/267; 260/293.53
[51] Int. Cl.² ...................................... C07D 455/02
[58] Field of Search .............. 260/293.53; 424/267

[56] References Cited

OTHER PUBLICATIONS

LaLonde et al., J. Amer. Chem. Soc., 1973, vol. 95, pp. 6342–6349.
Kuhn et al., Chem. Abst., 1959, vol. 53, cols. 22049–22050.
Chemical Abstracts: The Naming and Indexing of Chemical Compounds, from Chemical Abstracts, Introduction to the Subject Index of vol. 56, p. 89N (Jan.–June 1962).

Primary Examiner—Natalie Trousof
Attorney, Agent, or Firm—Cooper, Dunham, Clark, Griffin & Moran

[57] ABSTRACT

7-arylthiodeoxynupharidin-6-ols and 7-arylthioalkylenedeoxynupharidin-6-ols are useful for the control of certain pathogenic fungi.

8 Claims, No Drawings

PHENYL- AND 1-NAPHTHYL-THIODEOXYNUPHARIDIN-6-α-OLS

The invention described herein was made in the course of work under a grant or award from the Department of Health, Education and Welfare.

This invention is concerned with novel antimicrobial agents, compositions containing them, and their use. More particularly, it is concerned with certain 7-arylthiodeoxynupharidines and 7-arylthioalkylenedeoxynupharidines which because of their ability to control the growth of pathogenic microorganisms are useful in the control of mammalian diseases.

The compound nupharidine is a naturally occurring N-oxide which can be isolated from the rhizomes of *Nuphar luteum*. It can be converted to 6-dehydrodeoxynupharidine through Polonovski type eliminations with acetic anhydride or trifluoroacetic anhydride as described in the Journal of the American Chemical Society 93, 2501 (1971). The dehydro compound, on treatment with selected aryl, lower alkane, phenyl or naphthyl thiosulfonates is converted to a mixture of 7α- or 7β-arylthio substituted deoxynupharidines, the preferred compounds of the invention. These compounds are antimicrobial agents, particularly active against pathogenic fungi. Mixtures of the isomers can be employed, or the isomers can be separated for use. The 7β-compounds appear to be somewhat more stable.

The above identified article describes the preparation of 6-dehydrodeoxynupharidine as follows:

"(−)-Δ⁶-Dehydrodeoxynupharidine Using $(CF_3CO_2)_2O$. A solution of 1 g of nupharidine (4mmol) in 15 ml of dry methylene chloride was cooled to 0° and treated with 890 mg of trifluoroacetic anhydride (4.2 mmol) at 0° for 2 hr and at 25° for 80 hr under nitrogen. The methylene chloride was evaporated and the residue was basified with 10% methanolic potassium hydroxide. The methanol was evaporated and the residue triturated with ether. The ether solution was washed with water then dried ($Na_2SO_4$). Evaporation of the combined water wash solution afforded 396 mg of unconverted nupharidine. Evaporation of the ether gave 390 mg of crude Δ⁶-enamine identified by ir and nmr."

The arylthioalkylenedeoxynupharidines within the scope of the invention are prepared by treatment of 6-dehydrodeoxynupharidine with a haloalkyl aryl sulfide such as 2-bromoethyl phenyl sulfide.

While a number of 7α- and 7β-arylthio- and arylthioalkylenedeoxynupharidines have useful antimicrobial activity, the presently preferred compounds, which are preferred because they are relatively easy to produce and therefore economical, are those represented by the formulas:

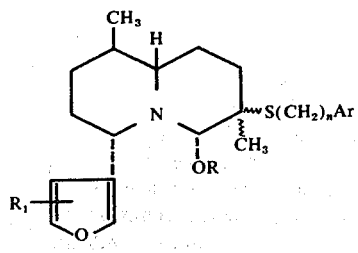

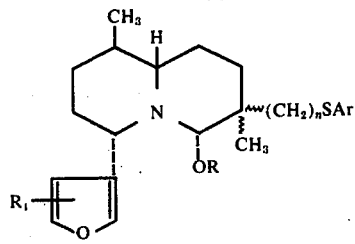

wherein:
n is an integer from 0 to 2;
R is hydrogen, alkyl containing up to eight carbon atoms, acyl containing up to eight carbon atoms;
$R_1$ is hydrogen, alkyl containing up to about 3 carbon atoms, aralkyl containing up to 10 carbon atoms in the aryl group and up to 3 carbon atoms in the alkyl group, carboxy, carbalkoxy containing up to 4 carbon atoms, amino, amido, hydroxy, alkoxy containing to 4 carbon atoms, keto containing up to 4 carbon atoms, aldehydo, halo, nitro, nitrilo, mercapto, thioalkoxy containing up to 4 carbon atoms and heterocyclic moieties;
Ar is a mono or bicyclic aryl group including substituted aryl groups wherein a substituent is selected from the group consisting of halogen, alkyl containing up to 6 carbon atoms, acyl containing up to 8 carbon atoms, amino, mono and dialkylamino wherein the alkyl groups which may be the same or different contain up to 6 carbon atoms, diphenylamino, alkylphenylamino wherein an alkyl group contains up to 6 carbon atoms, carboxy, carbalkoxy wherein an alkoxy group contains up to 6 carbon atoms, and (when n is at least 1) heterocyclic aryl wherein the heterocyclic moiety is pyridyl, furyl or thienyl.

The invention also includes ammonium, metallic and acid addition salts of the above identified compounds within its scope.

The 7-arylthio compounds of this invention are conveniently prepared by reaction between 6-dehydrodeoxynupharidine and an appropriate aryl substituted phenyl or naphthyl thiosulfonate such as phenyl benzenethiosulfonate, α- or β-naphthyl naphthalene thiosulfonate, or substituted phenyl and naphthyl benzene or naphthalene thiosulfonates such as:

1. tolyl toluenethiosulfonate
2. xylyl xylenethiosulfonate
3. o-dimethylaminophenyl o-dimethylaminobenzenethiosulfonate
4. p-diphenylaminophenyl p-diphenylaminobenzenethiosulfonate
5. m-diphenylaminophenyl m-diphenylaminobenzenethiosulfonate
6. o-methyl-p-carbomethoxyphenyl o-methyl-p-carbomethoxybenzenethiosulfonate
7. 2,4,6-trichlorophenyl 2,4,6-trichlorobenzenethiosulfonate
8. p-hexylphenyl p-hexylbenzenethiosulfonate
9. p-(N-hexyl)-acetamidophenyl p-(N-hexyl)-acetamidobenzenethiosulfonate
10. m-carbopentoxyphenyl m-carbopentozybenzenethiosulfonate
11. 2,3,6,8-tetramethyl-1-naphthyl 2,3,6,8-tetramethylnaphthalene-1-thiosulfonate
12. benzyl toluenethiosulfonate 13. 3-bromobenzyl benzenethiosulfonate
14. 2-chlorobenzyl benzenethiosulfonate
15. 2,4,5,7-tetrachloro-1-naphthyl 2,4,5,7-tetra chloronaphthalene-1-thiosulfonate
16. o-acetylphenyl o-acetylbenzenethiosulfonate
17. m-pentanoylphenyl m-pentanoylbenzenethiosulfonate
18. 5-phenyl-2-naphthyl 5-phenylnaphthalene-2-thiosulfonate
19. 6,7-diethyl-2-naphthyl 6,7-diethylnaphthalene-2-thiosulfonate
20. 2-pyridylmethyl benzenethiosulfonate
21. 2-methyl-3-pyridylmethyl toluenethiosulfonate
22. 2-thienylmethyl benzenethiosulfonate
23. 3-furylethyl toluenethiosulfonate
24. phenoxymethyl benzenethiosulfonate All of these compounds are known or can be prepared by known reactions; for example, by reaction of an aryl thiol with sulfuryl chloride, or by reaction of potassium or sodium benzene or toluenethiosulfonate with an appropriate aralkyl alkylating agent.

The arylthio compounds of the invention may also be prepared by reaction between 6-dehydrodeoxynupharidine and an appropriate aryl alkanethiosulfonate such as benzyl methanethiosulfonate. Such a compound may be prepared by treating benzyl bromide with potassium or sodium methanethiosulfonate.

The 7-arylthioalkylenedeoxynupharidines of this invention are prepared by reaction between a haloalkyl aryl sulfide and 6-dehydrodeoxynupharidine in a reaction inert, anhydrous, organic solvent in the presence of an alkaline reagent at an elevated temperature for from 2 to 6 hours.

Suitable solvents include liquid aromatic hydrocarbons containing up to 10 carbon atoms such as benzene, toluene or xylene. Alkaline reagents which are especially useful include alkali metal carbonates and bicarbonates, particularly sodium or potassium bicarbonate. The reaction temperature is normally from about 70° C to 100° C.

It is best to carry out the reaction in an inert atmosphere, suitably a nitrogen atmosphere.

As stated above, the scope of this invention includes compounds in which the furyl ring is substituted. Such compounds are prepared from deoxynupharidine by the sequence of reactions which include:
1. Substitution on the furyl ring
2. Oxidation to an N-oxide
3. Polonovski elimination
4. Conversion to 7-arylthio or 7-arylthioalkylene compounds by the reactions described above The furyl ring of deoxynupharidine can be acylated or nitrated by the procedure of Arata and Yamanouche as described in Yakugaku Zasshi, 91, 476 (1971). The acylated compound may be converted to an alkyl compound by a Wolff-Kishner reduction, or to a carboxy substituted compound by oxidation. The latter compound can be readily esterified by the usual esterification techniques. Amino substituted compounds are produced by reduction of nitro compounds.

The preparation of certain compounds within the scope of this invention require that precautions be taken to protect active hydrogen containing substituents such as carboxy, amino, or hydroxy substituents. The first mentioned group is readily protected by conversion to an ester. Amino any hydroxyl groups can be protected by acylation. The protective groups selected should be ones that are easily removed.

As will be recognized, certain of the compounds illustrated above are acidic or basic in nature. These can be readily converted to pharmaceutically acceptable ammonium, metallic or acid addition salts. It is specifically intended to include all such salts within the scope of this invention.

Typically useful metallic salts include alkali and alkaline earth metal salts of carboxy substituted compounds. Calcium, potassium and sodium salts are preferred. The preferred ammonium salts are tetraalkyl ammonium salts in which an alkyl group contains up to 4 carbon atoms. Typical examples of such compounds are calcium, potassium, sodium and tetraethyl ammonium salts of:

7$\beta$-(4-carboxyphenyl)-thiodeoxynupharidin-6$\alpha$-ol
7$\beta$-(2-carboxyphenylethyl)-thiodeoxynupharidin-6$\alpha$-ol
7$\beta$-(2,4-dicarboxynaphthyl)-thiodeoxynupharidin-6$\alpha$-ol
7$\beta$-(6,8-dicarboxy-2-naphthyl)-thiodeoxynupharidin-6$\alpha$-ol Typically useful acid addition salts include those derived by reaction of a pharmaceutically acceptable organic or inorganic acid with a primary, secondary or tertiary amino substituted arylthiodeoxynupharidin-ol. Such acids as hydrochloric, hydrobromic, sulfuric, nitric, phosphoric, acetic, propionic, glyconic, glutaric tartaric, citric, maleic and succinic are mentioned by way of example. These salts may be formed by reaction between the selected acid and a substrate such as 7$\beta$-(4-aminophenyl)-thiodeoxynupharidin-6$\alpha$-ol
7$\beta$-(2-dimethylaminonaphthyl)-thiodeoxynupharidin-6$\alpha$-ol
7$\beta$-(2,3-diaminophenyl)-thiodeoxynupharidin-6$\alpha$-ol
7$\beta$-[3,5-bis(dimethylamino)-2-naphthyl]-thiodeoxynupharidin-6$\alpha$-ol The 7-arylthio compounds of this invention are prepared by reaction in an inert solvent between the selected sulfonate thioester and 6-dehydrodeoxynupharidine. Typically useful organic solvents include hydrocarbon and halogenated hydrocarbon solvents, particularly aromatic hydrocarbon solvents such as benzene or toluene.

While a wide range of reaction temperatures from 0° C to 90° C or even higher can be tolerated in suitable cases, it is most advantageous and convenient to carry out the reaction at ambient temperature, say 20° C to 40° C since undesirable side reactions may take place at higher temperatures.

The reaction period will depend upon the selected temperature. In the range disclosed above, from 10 to 48 hours are normally adequate. At ambient temperatures, a time period of from 20 to 30 hours is preferred.

The reaction is best carried out in the presence of a suitable adsorbent which is effective to trap the intermediate immonium ion and thereby to prevent the occurrence of the reverse equilibrium reaction. The adsorbent is not essential however. A wide variety of adsorbents may be employed. These include, for example, aluminum oxide and partially hydrated aluminum oxide, as well as charcoal, powdered cellulose and magnesium silicate. The preferred adsorbent is partially hydrated aluminum oxide. Typically, the adsorbent is added in a weight range of from 2 to 10 times the weight of 6-dehydrodeoxy nupharidine.

It is desirable to carry out the reaction in an inert atmosphere to limit the possibility of undesirable side reactions. An atmosphere of nitrogen is generally most convenient, although helium could also be employed.

The reaction product is a mixture of the 7α- and the 7β-arylthio substituted compounds, for example, 7α-phenylthio-7-epideoxynupharidin-6β-ol and 7α-phenylthiodeoxynupharidin-6α-ol. These are readily separated by chemical or physical means, suitably chromotography using successively more polar solvents on an absorbent such as alumina. The β-compound normally separates first, but the effect of substituents on the aryl ring may reverse the normal separation order. It is not necessary to separate, since mixtures of the α- and β-isomers may be employed.

The products of this invention have an inhibitory effect on the growth of a variety of microorganisms including such human pathogenic fungi as (1) *Histoplasma capsulatum*, (2) *Blastomyces dermatitidis*, (3) *Trichophyton rubrum*, and (4) *Sporotrichum schenckii*.

The minimum in vitro inhibitory concentration of 7β-phenylthiodeoxynupharidin-6α-ol against these microorganisms in mcg/ml for a two week period as well as the disease and symptomatology usually associated with a mammalian infection by the microorganism is shown in Table 1.

TABLE 1

| Micro-organism | Conc. in mcg/ml | Disease | Symptomatology |
|---|---|---|---|
| 1 | 20 | Histoplasmosis | Cough, fever, emaciation, distress and difficulty in breathing, enlargement of hilar lymph glands, low leucocyte count, nodular red skin blotches, ulceration of naso-oral pharyngeal cavities and intestines, enlargement of spleen and liver. |
| 2 | 20 | Blastomycosis | Cough, chest pains, low grade fever, distress and difficulty in breathing, lung lesions, cutaneous lesions, inflammation of lymph vessels and enlargement of lymph nodes. |
| 3 | 80 | Dermatomycosis | Dermatitis, scalp lesions, scales on pubic and scalp hair, deterioration of nails. |
| 4 | 80 | Sporotrichosis | Subcutaneous nodules and cutaneous lesions, ulceration of naso-oral pharyngeal regions occasionally associated with angina, stomatitis, glossitis, laryngitis and rhinitis. |

The compounds of this invention may be used alone, but in the treatment of various diseases of man and animals, will normally be utilized in association with a pharmaceutically acceptable carrier. The selection of a carrier will depend on a variety of well recognized factors such as the reactivity of the physiologically active compound, the condition under treatment and the chosen route of administration.

For oral administration, the pharmaceutical compositions may be provided in the form of capsules and tablets including such excipients as starch, sugars and various forms of clay. Elixers and syrups may be provided as aqueous solutions or suspensions containing solubilizing, coloring, thickening or flavoring agents in accordance with standard practice. Parenteral dosage forms will normally be provided as isotonic solutions with physiological saline or glucose. For topical administration various pastes or oils, suitably a hydrocarbon fraction such as petrolatum, may serve as the carrier. In the various dosage unit forms, the compositions may contain from about 0.25 and 10% by weight, based on the total weight of the selected nupharidine derivative as the principal active ingredient.

The toxicity of the compounds of the invention is low in mice. Even at a level as high as 200 mg/Kg of body weight no toxic manifestations are observed with the compounds of this invention. This latter level represents a feeding to a mouse at a daily rate of 0.02% of its body weight. These results indicate that the products of this invention are substantially safe for use at all commonly employed dosage levels.

The novel compounds of this invention may be utilized as antimicrobial agents and may be administered in doses of from about 20 to 100 mg per kg of body weight per day. The physician or veterinarian in attendance will determine the optimum effective dosage and this will depend upon such factors as the age and weight of the patient, the condition under treatment including its stage of advancement, the selected route of administration and other factors well known to those skilled in the art.

The following non-limiting examples are given by way of illustration only.

EXAMPLE 1

7α-Phenylthio-7-epideoxynupharidin-6β-ol (7α-PTDOL) and

7β-Phenylthiodeoxynupharidin-6α-ol (7β-PTDOL)

A benzene solution (45 ml) containing 488 mg of 6-dehydrodeoxynupharidine, 541 mg of phenyl benzenethiosulfate and 2.5 g of neutral aluminum oxide (activity 3) was stored in the dark under nitrogen at 25° C for 16 hours. The reaction mixture was concentrated on the rotary evaporator and added to a 3 cm diameter column containing 60 g of neutral alumina (5% H$_2$O). The column was eluted successively with 200 ml hexane, 100 ml 10% hexane-benzene, 250 ml benzene, 200 ml 10% benzene-ether, 100 ml 66% benzene-ether and 150 ml methanol. Fractions A1, A2 and A5–A7 consisted of 35 ml each of hexane-benzene effluent with increasing proportions of benzene. Fractions A3 and A4 consisted of 60 ml each of $C_6H_6$. Fractions A8-A10 consisted of 35 ml each of 10% $C_6H_6$-ether. Combination of fractions A2 and A3 yielded 213 mg of pure liquid 7β-phenylthiodeoxynupharidin-6α-ol: tlc ($C_6H_6$) $R_f$ 0.3; ir (liquid film) 2.87 (OH), 6.32, 6.68 (Ar), 11.49 (3-furyl), 12.7, 13.4, 14.5 μ (Ar); pmr (60 MHz, $CDCl_3$), δ 0.92 (d, J = 3 Hz, 3H, C-1 $CH_3$), 1.14 (s, 3H, C-7 $CH_3$ ax), 2.60 (br m, 1H, C-10 H), 3.18 (br s, 1H, C-6 OH and disappearing on addition of $D_2O$), 3.77 (d of d, J = 5 and 9 Hz, 1H C-4 H), 4.07 (br s, 1H, C-6 H and sharpening on addition of $D_2O$), 6.24 (m, 1H, β-furyl H); 7.2–7.5 (m, 7H, phenyl and α-furyl H); ms m/e (% rel intensity) 357 (32) ($m^+$), 339 (7), 248 (100), 231 (25), 192 (247,164 (17), 150 (13), 147 (12), 135 (12), 110 (22), 107 (50), 94 (32), 81 (23), 79 (21), 77 (18); cd (c 0.35 mg/ml, neutral MeOH, 1 = 0.1 dm) $[\theta]_{300}$ ±0°, $[\theta]_{280}$ + 960, $[\theta]_{270}$ + 1710, $[\theta]_{264}$ + 2020, $[\theta]_{256}$ +2060, $[\theta]_{250}$ + 1760, $[\theta]_{240}$ + 600, $[\theta]_{236}$ ± 0, $[\theta]_{234}$ − 2520; cd (c 0.12 mg/ml, $HClO_4$ in MeOH, 1 = 0.1 dm) $[\theta]_{340}$ ± 0°, $[\theta]_{330}$ + 182, $[\theta]_{320}$ + 4240, $[\theta]_{310}$ + 7560, $[\theta]_{300}$ + 9680, $[\theta]_{295}$ + 10890, $[\theta]_{290}$ + 11800, $[\theta]_{285}$ + 14220, $[\theta]_{280}$ + 16300, $[\theta]_{275}$ + 18450, $[\theta]_{270}$ + 19360, $[\theta]_{265}$ + 19970, $[\theta]_{260}$ + 23000, $[\theta]_{256}$ + 29650, $[\theta]_{250}$ + 40540, $[\theta]_{246}$ + 44200, $[\theta]_{240}$ + 37500, $[\theta]_{234}$ + 30250, $[\theta]_{230}$ + 22400, $[\theta]_{225}$ + 16300, $[\theta]_{223}$ + 9680.

Fractions A8–A10 were combined to obtain 36 mg of pure 7α-phenylthio-7-epideoxynupharidin-6β-ol: tlc ($C_6H_6$) $R_f$ 0.09; ir (liquid film) 2.90 (OH), 6.0, 6.3 6.68 (Ar), 11.49 (3-furyl), 12.7, 13.4, 13.8, 14.8 μ (Ar); pmr (60 MHz $CDCl_3$) δ 0.94 (s, 6H with δ 0,96 d; C-7 $CH_3$ eq), 0.96 (d, J = 4.5 Hz, 6H with δ 0.94 s, C-1 $CH_3$), 2.38 (br m, C-10 H), 3.39 (br s, 1H, C-6 OH), 3.66 (t. J = 7 Hz, 1H, C-4 H), 4.40 (br s, 1H, C-6 H), 6.62 (m, 1H, β-furyl H), 7.2–7.6 (m, 7H, phenyl and α-furyl H); ms m/e (% rel intensity) 357 (10) ($M^+$), 339 (2), 265 (16), 248 (30), 246 (17), 231 (100), 218 (12), 204 (14), 194 (11), 192 (13), 176 (16), 164 (17), 150 (15), 148 (11), 136 (29), 130 (11), 122 (11), 121 (12), 110 (24), 109 (20), 108 (17), 107 (40), 96 (35), 95 (43), 94 (94), 81 (30), 79 (27), 78 (50 ); cd (c 0.40 mg/ml, neutral MeOH, 1 0.1 dm) $[\theta]_{380}$ ± 0°, $[\theta]_{360}$ + 150, $[\theta]_{340}$ + 220, $[\theta]_{320}$ + 310, $[\theta]_{310}$ + 130, $[\theta]_{302}$ ± 0, $[\theta]_{290}$ − 130, $[\theta]_{285}$ − 200, $[\theta]_{280}$ − 240, $[\theta]_{270}$ − 270, $[\theta]_{262}$ − 290, $[\theta]_{260}$ − 270, $[\theta]_{250}$ − 210, $[\theta]_{240}$ ± 0, $[\theta]_{238}$ + 530; cd (c 0.23 mg/ml, $HClO_4$ in MeOH, 1 0.1 dm) $[\theta]_{380}$ ± 0°, $[\theta]_{360}$ + 560, $[\theta]_{340}$ + 700, $[\theta]_{330}$ + 310, $[\theta]_{320}$ − 620, $[\theta]_{310}$ − 2340, $[\theta]_{300}$ − 4050, $[\theta]_{295}$ + 4520, $[\theta]_{290}$ − 4360, $[\theta]_{280}$ − 3740, $[\theta]_{276}$ − 3430, $[\theta]_{270}$ − 3900, $[\theta]_{264}$ − 5200, $[\theta]_{260}$ − 6540, $[\theta]_{255}$ − 8100, $[\theta]_{250}$ − 9690, $[\theta]_{248}$ − 9520, $[\theta]_{240}$ − 8340, $[\theta]_{230}$ − 5610.

Fractions A4–A7 (combined, 264 mg) consisted of mixtures 7α-phenylthio-7-epideoxynupharidine-6β-ol and 7β- phenylthiodeoxynupharidine-6α-ol. Rechromatography as above gave 78 mg of the former and 93 mg of the latter.

EXAMPLE 2

Immonium Perchlorate Salt from 7β-Phenylthiodeoxynupharidin-6α-ol

A solution of 54 mg of 7-β-phenylthiodeoxynupharidin-6α-ol in 2 ml of abs. EtOH was treated with 0.76 ml of 0.2 M aqueous $HClO_4$. The resulting white solid was recrystallized from acetone; thereby was obtained 50 mg of white crystalline immonium perchlorate: mp 241°–244°; ir (KBr) 5.98 (s, C = $N^+$), 6.26 (Ar), 6.69 (Ar), 11.49 (3-furyl), 12.32, 12.41, 13.04, 13.38, 14.38, 14.50 μ; pmr (60 Hz, $CDCl_3$), δ 1.03 (d, J = 5.5 Hz, 3H, C-1 $CH_3$), 1.38 (s, 3H, C-7 $CH_3$), 3.67 (br m, 1H, C-10 H), 5.05 (d of d, J = 6.5 and 14.5 Hz, 1H, C-4 H), 6.62 (q, J = 1 Hz, β-furyl H), 7.38 (m, 5H, phenyl H); 7.58 (br s, 1H, α-furyl or C-6 H), 7.72 (t, J − 1.5 Hz, 1H, α-furyl H), 7.81 (br s,1H, α-furyl or C-6 H); cmr δ 18.37 (C-11, eq $CH_3$), 22.51 (C-16, $CH_3$ ax), 24.60 (C-9), 28.69 (C-8), 32.89 (C-2 and 3), 38.60 (C-1), 48.89 (C-7), 67.10 (C-10 or 4), 68.70 (C-4or 10), 111.19 (C-13), 119.54 (C-12), 128.03 (C-1'), 131.01 (C-2'), 132.31 (C-4'), 139.04 (C-3'), 145.96 (C-15), 147.11 (C-14), 172.64 (C-6).

Anal. Calcd for $C_{21}H_{26}NO_5SCl$: C, 57.32; H, 5.97; N, 3.18; S, 7.29. Found: C, 57.18; H, 6.11; N, 3.22; S, 7.23.

EXAMPLE 3

6α-Acetoxy-7β-phenylthiodeoxynupharidine

To a dioxane solution (1.3 ml) containing 36 mg 7β-phenylthiodeoxynupharidin-6α-ol is added 6.0 mg of glacial acetic acid at 25° C. Thereafter the dioxane is removed by vacuum evaporation to obtain a mixture of 6α-acetoxy-7β-phenylthiodeoxynupharidine and the immonium acetate of 7β-phenylthiodeoxynupharidin-6α-ol.

EXAMPLE 4

6α-Ethoxy-7β- phenylthiodeoxynupharidine

A severalfold excess of anhydrous ethanol is added to 11 mg of 7β-phenylthiodeoxynupharidin-6α-ol and the ethanol is removed by vacuum evaporation. The addition of ethanol and vacuum evaporation is repeated three times. The residue consists of 6α-ethoxy-7β-phenylthiodeoxynupharidine.

EXAMPLE 5

6α-Benzoxy-7β-phenylthiodeoxynupharidine -(m-methoxybenzyl)-thiodeoxynupharidin- In a manner similar to that described in Example 4, 10 mg of 7β-phenylthiodeoxynupharidin-ol is treated with benzyl alcohol. Thereby is obtained 6α-benzoxy-7β-phenylthiodeoxynupharidine.

EXAMPLE 6

7α-(m-Methoxybenzyl)-thio-7-epideoxynupharidin-6β-ol and 7β-(m-Methoxybenzyl)-thiodeoxynupharidin-6α-ol An anhydrous benzene solution (25 ml) containing 231 mg of 6-dehydrodeoxynupharidine, 369 mg of m-methoxybenzyl p-toluenethiosulfonate and 2 g of suspended neutral aluminum oxide (activity 3) is stored in the dark under nitrogen at 25° for 20 hrs. The reaction mixture then is processed and separated as in Example 1 and thereby 7α-(m-methoxybenzyl)-thio-7-epideoxynupharidin-6β-ol and 7β-(m-methoxybenzyl)-tbhiodeoxynupharidin-6α-ol are obtained.

EXAMPLE 7

7α-(1-Naphthyl)-thio-7-epideoxynupharidin-6β-ol and 7β-(1-Naphthyl)-thiodeoxynupharidin-6α-ol -(m-methoxybenzyl)-thiodeoxynupharidin- An anhydrous toluene solution (70 ml) containing 150 mg of 6-dehydrodeoxynupharidine, 193 mg of 1-naphthyl 1-naphthalenethiosulfonate and 1 g of suspended neutral aluminum oxide (activity 2) is stored in the dark under nitrogen at about 15° for 52 hr. The reaction mixture then is processed and separated as in Example 1 and thereby 7α-(1-naphthyl)-thio-7-epideoxynupharidin-6β-ol and 7β-(1-naphthyl)-thiodeoxynupharidin-6α-ol are obtained.

EXAMPLE 8

7α-Phenoxymethylthio-7-epideoxynupharidin-6β-ol and 7β-Phenoxymethylthiodeoxynupharidin-6α-ol An anhydrous benzene solution (40 ml) containing 693 mg of 6-dehydrodeoxynupharidine, 1 g of phenoxymethyl toluenethiosulfonate and 500 mg of suspended powdered cellulose is stored in the dark under nitrogen at 25° for 48 hrs. The reaction mixture then is processed and separated as in Example 1 and thereby 7α-phenoxymethylthio-7-epideoxynupharidin-6β-ol and 7β-phenoxymethylthiodeoxynupharidin-6α-ol are obtained.

EXAMPLE 9

7α-[p-(N-methyl)-acetamidophenyl]-thio-7-epideoxynupharidin-6β-ol and
7β-[p-(N-methyl)-acetamidophenyl]-thiodeoxynupharidin-6α-ol A flask containing 231 mg of p-(N-methyl)-acetamidophenyl p-(N-methyl)-acetamidobenzenethiosulfonate, 405 mg of 6-dehydrodeoxynupharidine and 100 mg of powdered charcoal is repeatedly vacuum evacuated and purged with helium at 25° C. A 60 ml quantity of xylene is distilled under helium into the reaction flask and the resulting mixture is stirred rapidly and warmed to 80° C under helium. After 12 hrs. at 80° C, the flask is cooled and its contents are processed and separated as in Example 1 to obtain the separate title compounds.

EXAMPLE 10

7α-(p-Carbethoxyphenyl)-7-epideoxynupharidin-6β-ol and
7β-(p-Carbethoxyphenyl)-thiodeoxynupharidin-6α-ol An anhydrous benzene solution (40 ml) containing 950 mg of 6-dehydrodeoxynupharidine, 1.6 g of p-carbethoxyphenyl p-carbethoxybenzenethiosulfonate and 4 g of suspended aluminum oxide (activity 4) is stored in the dark under nitrogen at 25° C for 26 hrs. The reaction mixture then is processed and separated as in Example 1 to obtain the separate title compounds.

EXAMPLE 11

7α-2-phenylpropylthio-7-epideoxynupharidin-6β-ol and 7β-2-phenylpropylthiodeoxynupharidin-6α-ol An anhydrous benzene solution (45 ml) containing 231 mg of 6-dehydrodeoxynupharidine, 307 mg of phenylpropyl benzenethiosulfonate and 1.5 g of suspended neutral aluminum oxide (activity 3) is stored in the dark under nitrogen at 10° C for 45 hours. The reaction mixture then is processed as in Example 1.

EXAMPLE 12

The Potassium Salt from
7β-(p-Carboxyphenyl)-thiodeoxynupharidin-6α-ol

A methanol-water solution of 7β-(p-carbethoxyphenyl)-thiodeoxynupharidin-6α-ol is warmed with a 5% excess of potassium carbonate under nitrogen for 4 hours. Thereafter, the unconsumed potassium carbonate is neutralized with hydrochloric acid, and the solvent is vacuum evaported to obtain the potassium salt of 7β-(p-carboxyphenyl)-thiodeoxynupharidin-6α-ol.

EXAMPLE 13

The Immonium Chloride Salt of
7β-(p-Carboxyphenyl)-thiodeoxynupharidin-6α-ol

The reaction mixture described in Example 11 is acidified with hydrochloric acid to a pH of about 4. Thereafter the solvent is vacuum evaporated to obtain the immonium chloride salt of 7β-(p-carboxyphenyl)-thiodeoxynupharidin-6α-ol.

EXAMPLE 14

The Immonium-ammonium Dichloride from
7β-[p-(N-methyl)-aminophenyl]-thiodeoxynupharidin-6α-ol A dioxane-water solution of 7β-[p-(N-methyl)-acetamidophenyl]-thiodeoxynupharidin-6α-ol and a 10% excess of hydrochloric acid is stored at 65° C under nitrogen for 24 hrs. Thereafter the vessel is cooled and the solvent vacuum evaporated. The residue is the title compound.

EXAMPLE 15

7α-Phenylthioethylene-7-epideoxynupharidin-6β-ol and 7β-Phenylthioethylenedeoxynupharidin-6α-ol An anhydrous benzene solution (90 ml) containing 600 mg of 6-dehydrodeoxynupharidine and a 20% molar excess of 2-bromoethyl phenyl sulfide together with 0.5 g of solid sodium bicarbonate is maintained at 80° C to 90° C for 4 hours under nitrogen. An equal volume of ether is added, and the mixture is shaken with 50 ml of 5% aqueous potassium hydroxide solution. The organic layer is separated, dried over anhydrous sodium sulfate, filtered and evaporated to dryness. The mixture is then processed and separated as in Example 1.

EXAMPLE 16

Antifungal Activity

Antifungal Activity — Procedure and Results: Preparation of a solution of 7β-PTDOL suitable for running the antifungal tests was carried out in the following manner. A 50 mg sample of 7β-PTDOL was dissolved in a mixture of 30 mg of acetic acid and 5.5 ml of dimethylsulfoxide. The resulting homogeneous solution was then diluted to 50 ml with water and thereafter employed to inhibit the growth of the microorganisms in vitro. The reference solvent which was used for comparison purposes was made up in a similar manner. Thus 60 mg of acetic acid and 11 ml of dimethylsulfoxide was diluted to 103 ml with water. These solutions of 7β-PTDOL and reference solvent were sterilized by filtering through a Seitz filter.

The mycelial growth of *Blastomyces dermatitidis* and *Histoplasma capsulatum* was inhibited up to the end of two weeks by concentrations of 20 μg/ml of 7β-PTDOL in Sabouraud dextrose agar. Table 2 shows that growth was inhibited for longer periods at higher concentrations of 7β-PTDOL in Sabouraud dextrose agar. Additionally, the mycelial growth of *Sporotrichum schenckii* and *Tricophyton rubrum* was hihibited up to the end of two weeks by concentrations of 80

μg/ml of 7β-PTDOL in Sabouraud dextrose agar. These results are given in Table 3.

EXAMPLE 17

A liquid pharmaceutical composition was prepared by combining the following ingredients in the proportions by weight specified.

| | |
|---|---|
| Active compound | 20 |
| Citric acid | 20 |
| Saccharin | 3 |
| Imitation wild cherry flavor | 2 |
| Ethanol (95%) | 25 |
| Water | 30 |

The liquid formulation is thoroughly mixed to provide an elixer containing approximately 200 mg of the active ingredient per gram of solution.

The following compounds were utilized to prepare the compositions of this example:

7β-phenylthiodeoxynupharidin-6α-ol

7β-(p-chlorophenyl)-thiodeoxynupharidin-6α-ol

7β-(m-clorophenyl)-thiodeoxynupharidin-6α-ol

7β-(p-carbomethoxyphenyl)-thiodeoxynupharidin-6α-ol

7β-(1-naphthyl)-thiodeoxynupharidin-6α-ol

EXAMPLE 18

Separate dry solid pharmaceutical compositions are prepared by separately blending the compounds of Example 17 in the proportions by weight specified.

| | |
|---|---|
| Active compound | 50 |
| Sodium citrate | 25 |
| Alginic acid | 10 |
| Polyvinylpyrrolidone | 10 |
| Magnesium stearate | 5 |

After each dried composition is thoroughly blended, tablets are punched out, each tablet being of a size that it contains 100 mg of active ingredient.

EXAMPLE 19

Separate dry solid pharmaceutical compositions are prepared by separately blending the compounds of Example 17 in the proportions by weight specified.

| | |
|---|---|
| Active compound | 50 |
| Calcium carbonate | 20 |
| Polyethylene glycol (average molecular weight 4,000) | 30 |

The dried solid mixtures so prepared are thoroughly agitated so as to obtain completely uniform powdered products. Soft elastic and hard sealed gelatin capsules containing these pharmaceutical compositions are prepared employing a sufficient quantity of material so as to furnish 250 mg of active ingredient in each capsule.

TABLE 2

Sensitivities of *Histophasma capsulatum* and *Blastomyces dermatitidis* to 7β-PTDOL as Expressed by Weekly Increments of the Diameter of Colony (in Millimeters) on Sabouraud Dextrose Agar at 25° C (Mycelial Phase)[a]

| Concentration of 7β-PTDOL Mcg/Ml | H. capsulatum | | | | | | | | B. dermatitidis | | | | | | | |
|---|---|---|---|---|---|---|---|---|---|---|---|---|---|---|---|---|
| | Isolate 1098 | | | | Isolate 1106 | | | | Isolate 1099 | | | | Isolate 1107 | | | |
| | Wk 1 | 2 | 3 | 4 | 1 | 2 | 3 | 4 | 1 | 2 | 3 | 4 | 1 | 2 | 3 | 4 |
| 100 | 0[b] | 0 | 0 | 0 | 0 | 0 | 0 | 0 | 0 | 0 | 0 | .3 | 0 | 0 | 8 | 12 |
| 80 | 0 | 0 | 0 | 0 | 0 | 0 | 0 | 0 | 0 | 0 | T[c] | 5 | 0 | 0 | 8 | 13 |
| 60 | 0 | 0 | 0 | 0 | 0 | 0 | 0 | 0 | 0 | 0 | T | 6 | 0 | 0 | 7 | 12 |
| 40 | 0 | 0 | 0 | 2 | 0 | 0 | 0 | 5 | 0 | 0 | 7 | 11 | 0 | 0 | 11 | 16 |
| 20 | 0 | 0 | 5 | 11 | 0 | 0 | 6 | 16 | 0 | 0 | 11 | 12 | 0 | T | 15 | 24 |
| 10 | T | T | 8 | 16 | 0 | 0 | 7 | 19 | 0 | T | 14 | 20 | 0 | T | 17 | 31 |
| Solvent Control | 3 | 5 | 14 | 27 | 4 | 6 | 15 | 26 | T | 11 | 29 | 40 | T | 12 | 35 | 40 |
| Control | 5 | 5 | 16 | 27 | 5 | 5 | 18 | 33 | T | 12 | 28 | 40 | T | 11 | 35 | 40 |

[a] All measurements are from the average of two cultures
[b] 0: no growth
[c] T: trace of growth Example 17 in the proportions by weight specified.

TABLE 3

Sensitivities of *Sporotrichum schenckii* and *Tricophyton rubrum* to 7β-PTDOL as Expressed by Weekly Increments of the Diameter of Colony (in Millimeters) on Sabouraud Dextrose Agar at 25° C (Mycelial Phase)[a]

| Concentration of 7β-PTDOL Mcg/Ml | S. schenckii | | | | T. rubrum | | | |
|---|---|---|---|---|---|---|---|---|
| | Isolate 1109 | | | | Isolate 1112 | | | |
| | Wk 1 | 2 | 3 | 4 | 1 | 2 | 3 | 4 |
| 100 | 0 | T | 3 | 7 | 0 | 0 | 5 | 11 |
| 80 | 0 | T | 4 | 9 | 0 | 0 | 7 | 15 |
| 60 | 0 | 3 | 5 | 9 | T | T | 8 | 17 |
| 40 | 0 | 2 | 5 | 11 | T | 2 | 10 | 23[d] |
| 20 | 0 | 3 | 7 | 16 | T | 3 | 14 | 28[d] |
| 10 | 0 | 4 | 9 | 16 | 3 | 3 | 15 | 26[d] |
| Solvent Control | 6 | 6 | 15 | 24 | 5 | 5 | 19[d] | 31[d] |

TABLE 3-continued

Sensitivities of
*Sporotrichum schenckii* and *Tricophyton rubrum*
to 7β-PTDOL as Expressed by Weekly Increments of the
Diameter of Colony (in Millimeters) on
Sabouraud Dextrose Agar at 25° C (Mycelial Phase)[a]

| Concentration of 7β-PTDOL Mcg/Ml | S. schenckii Isolate 1109 | | | | T. rubrum Isolate 1112 | | | |
|---|---|---|---|---|---|---|---|---|
| | Wk 1 | 2 | 3 | 4 | 1 | 2 | 3 | 4 |
| Control | 6 | 8 | 19 | 29 | 5 | 5 | 17[d] | 20[d] |

[a] All measurements are from the average of two cultures
[b] 0: no growth
[c] T: trace of growth
[d] Overgrown by adjacent colony of *M. gypseum*

What is claimed is:
1. A compound selected from the group consisting of:
   7β-Phenylthiodeoxynupharidin-6α-ol,
   7β-(p-Chlorophenyl)-thiodeoxynupharidin-6α-ol,
   7β-(m-Chlorophenyl)-thiodeoxynupharidin-6α-ol,
   7β-(p-Carbomethoxyphenyl)-thiodeoxynupharidin-6α-ol, and
   7β-(1-Naphthyl)-thiodeoxynupharidin-6α-ol.
2. 7β-Phenylthiodeoxynupharidin-6α-ol.
3. 7β-(p-Chlorophenyl)-thiodeoxynupharidin-6α-ol.
4. 7β-(m-Chlorophenyl)-thiodeoxynupharidin-6α-ol.
5. 7β-(p-Carbomethoxyphenyl)-thiodeoxynupharidin-6α-ol.
6. 7β(1-Naphthyl)-thiodeoxynupharidin-6α-ol.
7. A therapeutic composition containing a fungistatically effective amount of a compound of claim 1 together with a pharmaceutically acceptable carrier.
8. A method of inhibiting the growth of *Histoplasma capsulatum*, *Blastomyces dermatitidis*, *Trichophyton rubrum* or *Sporotrichum schenckii* by administering to a locus affected therewith a fungistatically effective amount of a compound of claim 1.

* * * * *